(12) United States Patent
Chen et al.

(10) Patent No.: US 11,981,697 B2
(45) Date of Patent: May 14, 2024

(54) METHOD FOR PREPARING DELPHINIUM ACYLATED ANTHOCYANIN

(71) Applicant: ZHEJIANG UNIVERSITY, Zhejiang (CN)

(72) Inventors: Wei Chen, Hangzhou (CN); Jiahong Xie, Hangzhou (CN); Yang Xu, Hangzhou (CN); Haoxin Cui, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 338 days.

(21) Appl. No.: 17/674,860

(22) Filed: Feb. 18, 2022

(65) Prior Publication Data

US 2022/0194979 A1 Jun. 23, 2022

Related U.S. Application Data

(63) Continuation of application No. PCT/CN2021/070637, filed on Jan. 7, 2021.

(30) Foreign Application Priority Data

Sep. 14, 2020 (CN) .......................... 202010961060.5

(51) Int. Cl.
*C07H 17/065* (2006.01)
*B01D 11/02* (2006.01)
(Continued)

(52) U.S. Cl.
CPC ....... *C07H 17/065* (2013.01); *B01D 11/0265* (2013.01); *B01D 15/426* (2013.01); *C07H 1/08* (2013.01)

(58) Field of Classification Search
None
See application file for complete search history.

(56) References Cited

U.S. PATENT DOCUMENTS

2024/0025937 A1* 1/2024 Chen .................... C07H 17/065

FOREIGN PATENT DOCUMENTS

| CN | 102229633 A | 11/2011 |
| CN | 102391334 A | 3/2012 |

(Continued)

OTHER PUBLICATIONS

Costa et al., "Strategies of solvent system selection for the isolation of flavonoids by countercurrent chromatography" J Sep Sci vol. 33 pp. 336-347 DOI 10.1002/jssc.200900632 (Year: 2010).*

(Continued)

*Primary Examiner* — Eric Olson
(74) *Attorney, Agent, or Firm* — W&G Law Group

(57) ABSTRACT

Disclosed is a method for separating and preparing delphinidin-3-O-(6"-O-p-coumaroyl) glucoside. By means of extraction, macroporous resin purification, extraction, preparative liquid chromatography and high-speed countercurrent chromatography and the like, a high-purity delphinidin-3-O-(6"-O-p-coumaroyl) glucoside monomer can be obtained from grapes by separation and purification. By means of this method, at least 80 mg of delphinidin-3-O-(6"-O-p-coumaroyl) glucoside can be obtained from 10 kg of grape skins, with the purity can be no less than 98%. The method has the advantages of simple operation, large handling capacity, good repeatability, etc., which provides a new idea for the development and utilization of grape resources.

7 Claims, 4 Drawing Sheets

(51) Int. Cl.
  *B01D 15/42*  (2006.01)
  *C07H 1/08*  (2006.01)

(56) References Cited

FOREIGN PATENT DOCUMENTS

| | | |
|---|---|---|
| CN | 102796154 A | 11/2012 |
| CN | 104177460 A | 12/2014 |
| CN | 107522761 A | 12/2017 |
| CN | 108409805 A | 8/2018 |
| CN | 112175028 A | 1/2021 |
| WO | 2007125562 A2 | 11/2007 |
| WO | 2015127118 A1 | 8/2015 |

OTHER PUBLICATIONS

Zhao et al., "An effective method for the semi-preparative isolation of high-purity anthocyanin monomers from grape pomace" Food Chemistry vol. 310 125830 DOI 10.1016/j.foodchem.2019.125830 (Year: 2020).*

Dong et al., "A general separation method of phenolic acids using pH-zone-refiningcounter-current chromatography and its application to oat bran" Journal of Chromatography B vo. 992 pp. 36-42, DOI 10.1016/j.jchromb.2015.04.024 (Year: 2015).*

Li et al., "Separation and purification of polyphenols from red wine extracts using high speed counter current chromatography" Journal of Chromatography B vol. 1054 pp. 105-113 DOI 10.1016/j.jchromb.2017.03.006 (Year: 2017).*

Fanzone et al., "Phenolic Characterization of Malbec Wines from Mendoza Province (Argentina)" J Agric Food Chem vol. 58 pp. 2388-2397 DOI:10.1021/jf903690v (Year: 2010).*

International Search Report (PCT/CN2021/070637); Date of Mailing: Jun. 18, 2021.

CN First Office Action(202010961060.5); Date of Mailing: Jul. 28, 2021.

Comprehensive Characterization of Extractable and Nonextractable Phenolic Compounds by High-Performance Liquid Chromatography-Electrospray Ionization-Quadrupole Time-of-Flight of a Grape/Pomegranate Pomace Dietary Supplement; Date of Mailing: Dec. 27, 2017.

* cited by examiner

METHOD FOR PREPARING DELPHINIUM ACYLATED ANTHOCYANIN

CROSS-REFERENCE TO RELATED APPLICATION

This application is a continuation application of International Application No. PCT/CN2021/070637, filed on PCT on Jan. 7, 2021, which claims priority to Chinese Application No. 202010961060.5, filed on Sep. 14, 2020, both of which are incorporated by reference herein.

TECHNICAL FIELD

The present application relates to the technical field of separation and purification of natural products, particularly the method for separating and preparing delphinidin-3-O-(6"-O-p-coumaroyl) glucoside.

BACKGROUND

Grapes (*Vitis vinifera* L.) are popular fruit which are wildly cultivated all over the world. Anthocyanins are one of the important class of polyphenols in grapes. Studies have shown that grapes contain anthocyanins, which are formed by the combination of anthocyanin aglycones such as delphinidin, malvidin, peonidin and petunidin as well as glucoside. However, anthocyanins are sensitive to light, temperature and pH, and show relatively low bioavailability, which greatly limits the practical application. Studies have shown that acylated anthocyanins have higher stability, bioavailability, and biological activity in comparison with non-acylated anthocyanins. Grapes is rich in coumaroylated anthocyanins, which indicates that grape anthocyanins have a better market prospect.

Novel purification technologies such as solid phase extraction (SPE), preparative-high performance liquid chromatography (preparative-HPLC) and high-speed countercurrent chromatography (HSCCC) have begun to be developed and applied in recent years. High performance liquid chromatography is a chromatographic technology based on the principle of solid-liquid adsorption using adsorbents such as silica gel, and the separation is based on the difference in the binding ability of different compound with the stationary phase. The separation effect mainly depends on the properties of a stationary phase (such as composition and particle size), and the liquid chromatography methods. The high performance liquid chromatography technology has the advantages of good stability, reliability and repeatability. Countercurrent chromatography is a liquid-liquid chromatography technology in which the stationary phase and mobile phase are both liquid. The principle is to separate different compounds based on the difference of partition coefficients between the stationary phase and mobile phase. Therefore, the separation effect of countercurrent chromatography mainly depends on the selection of two-phase solvent system. The countercurrent chromatography technology has the advantages including simple sample pretreatment, wide application range, less sample loss, and large handling capacity. Nowadays for the preparation of the grape anthocyanins, the extraction, macroporous resin, and a single column chromatography or chromatographic technology are mainly used for separation and purification.

For example, CN104177460A discloses a method for preparing 3, 5-disaccharide anthocyanin. The method used the ultrasonic-assisted extraction, solvent extraction, purification and other steps, but the obtained product was an anthocyanin mixture of three different disaccharide anthocyanins, and the product did not contain acylated anthocyanins.

For example, CN102229633A discloses a method for separating and preparing five high-purity anthocyanin monomers from grape skins. This method used the extraction, macroporous resin purification, and preparative-HPLC purification for obtaining five anthocyanins. However, due to the use of two steps of preparative HPLC purification, the sample was lost, and the purified-yield was reduced. The purity of two acylated anthocyanins (malvidin 3-(6"-acetyl-glucoside), and malvidin 3-(6"-p-coumarylglucoside)) was relatively low, with only 91.7% and 95.5%, respectively.

CN108976268A discloses a method for preparing two main anthocyanin standard products of brier grapes. The method introduced using macroporous resin to adsorb and enrich brier grape juice, and then performing elution and freeze drying to obtain a crude anthocyanin product. After that, they used high speed countercurrent chromatography and using water, n-butanol, methyl tert-butyl ether, acetonitrile and trifluoroacetic acid (at a volume ratio of 5:4:1:2: 0.001 or 5:3:1:1:0.001) as a two-phase solvent system for separating and obtaining two anthocyanins with purity of 95.8% and 92.2%, respectively. However, it can be seen from an HPLC chromatogram that the anthocyanins composition of the brier grape is simple. It can be inferred from the limitations of high speed countercurrent chromatography that, when the anthocyanins of the separated samples are complex, it may be difficult to obtain the target anthocyanin by using this method.

Due to the difficulty in separation and purification of the acylated anthocyanins, there are currently no commercial acylated anthocyanin on the market. Therefore, this work develop a new process to purify the acylated anthocyanin monomer (delphinidin-3-O-(6"-O-p-coumaroyl) glucoside) from raw materials (such as grapes)-derived complex anthocyanin, which is of great significance to promote the standard anthocyanin market and to develop deep-processed grape products.

SUMMARY

In view of the shortcomings in the field, the present application provides a method for the separation and preparation of delphinidin-3-O-(6"-O-p-coumaroyl) glucoside, which provides new opportunities for the development and utilization of grape resources.

A method for separating and preparing delphinidin-3-O-(6"-O-p-coumaroyl) glucoside includes:
- alcohol extraction and concentration: using grapes as a raw material, and extracting by an acid ethanol solution, filtering and concentrating to obtain a crude grape skin anthocyanin extract;
- macroporous resin purification: injecting the crude grape skin anthocyanin extract into macroporous resin, and eluting and concentrating to obtain an anthocyanin eluent;
- extraction: extracting the anthocyanin eluent with an organic solvent, concentrating under reduced pressure, and freeze-drying to obtain anthocyanin lyophilized powder;
- purification by preparative liquid chromatography: dissolving the lyophilized anthocyanin powder, injecting the solution into a preparative liquid chromatography system for purification, and detecting it with an ultraviolet detector, wherein the specific conditions are as follows:

mobile phase: The mobile phase consists of acetonitrile (phase A) and 1%-2% (v/v) aqueous formic acid solution (phase B);

the gradient elution program is: 0 min-4 min, 5%-20% phase A; 4 min-18 min, 20%-25% phase A; 18 min-21 min, 25%-35% phase A; 21 min-24 min, 35%-60% phase A; 24 min-27 min, 60%-5% phase A; 27 min-30 min, 5% phase A;

the flow rate is 8 mL/min-10 mL/min, the column temperature is 30° C., and the detection wavelength is 520 nm;

collecting components with a retention time of 16.5 min-18.0 min according to the liquid chromatogram, concentrating under reduced pressure and freeze-drying to obtain a crude product of anthocyanin monomer; and separation by high-speed countercurrent chromatography: mixing methyl tert-butyl ether, methanol, water and trifluoroacetic acid at a volume ratio of 2:2:3:0.001 to as a two-phase solvent system, using the upper phase as a stationary phase, and using the lower phase as a mobile phase, pumping the stationary phase and the mobile phase into a high-speed countercurrent chromatographic instrument in turn, after the two phases reach balance in a pipeline, dissolving the crude product of anthocyanin monomer in the mobile phase, injecting the sample, and detecting by the ultraviolet detector, wherein the detection wavelength is 280 nm, collecting the fractions with a retention time of 105 min-115 min, concentrating under reduced pressure, and freeze-drying to obtain a target compound delphinidin-3-O-(6"-O-p-coumaroyl) glucoside.

Unless otherwise specified, the percentages of raw materials in the present application all refer to volume percentage concentration. All solutions in the present application, unless otherwise specified, all use water as the solvent.

The extracting by an acid alcohol solution, filtering and concentrating to obtain the crude anthocyanin extract of grape skins includes: washing the grapes and peeling them, mixing the grape skins with an acid ethanol solution and pulping, ultrasonic extracting below 50° C. (preferably at room temperature) and filtrating, and concentrating the filtrate under reduced pressure at 40° C.-50° C. for removing ethanol, so as to obtain the crude anthocyanin extract of grape skins; wherein, a material-to-liquid ratio of the grape skins to the acid ethanol solution is 1 g:4 mL-8 mL; in the acid ethanol solution, the volume concentration of ethanol is 50%-80%, preferably 60%-70%, and the volume concentration of the acid is 0.1%-1%; and the ultrasonic extraction time is 40 min-120 min.

In the acid ethanol solution, the acid is selected from at least one of hydrochloric acid, formic acid, or acetic acid.

The method of the macroporous resin purification includes:

injecting the crude grape skin anthocyanin extract into the macroporous resin, eluting by sequentially using acid ethanol solutions in which the volume concentration of ethanol is 0, 5%, 20% and 40% each at a dose of 4 times the bed volume (4 BV), collecting acid ethanol eluent in which the volume concentration of ethanol is 40%, and evaporating under reduced pressure at 40° C.-50° C. for removing ethanol to obtain the anthocyanin eluent, wherein the macroporous resin is selected from AB-8, D101, XAD-7, HPD-100 or DM-130, with a specific surface area of 450 m²/g-550 m²/g, an average pore diameter of 10 nm-50 nm, and a particle size range of 0.3 mm-1.25 mm; and the acid ethanol solution is selected from ethanol solutions in which the volume percent concentration of the acid is 0.1% to 1.5%, wherein the acid is selected from at least one of hydrochloric acid, formic acid, or acetic acid.

The organic solvent used in the step "extration" is ethyl acetate.

Preferably, a volume ratio of the organic solvent to the anthocyanin eluent of 1:1 is adopted for extraction, and for twice or more.

In the step "purification by preparative liquid chromatography", the lyophilized anthocyanin powder can be dissolved by the phase B or water.

In the step "purification by preparative liquid chromatography", the liquid chromatographic column used by the preparative liquid chromatography system is a C18 column, and the single injection is 10 mg-40 mg based on the lyophilized anthocyanin powder, and the volume after concentration under reduced pressure is 40%-70% of the volume before concentration.

In the step "separation by high-speed countercurrent chromatography", the temperature of the high-speed countercurrent chromatographic instrument is stabilized at 20° C.-30° C., it is at the forward-inlet elution mode, and pumping the stationary phase, and the rotating speed is adjusted to 800 r/min-950 r/min, the mobile phase is introduced at a flow rate of 2 mL/min and allowed to be balanced, and the single injection is 30 mg-200 mg based on the crude product of anthocyanin monomer.

Compared with the prior art, the main advantages of the present application include:

1. A method for separating the delphinidin-3-O-(6"-O-p-coumaroyl) glucoside (the molecular structure is shown in FIG. 1) from grape skins is established for the first time, the yield can reach not less than 8 mg/kg of grape skins, and the purity can reach not less than 98%.

2. By combining the preparative liquid chromatography with the high-speed countercurrent chromatography, a large amount of delphinidin-3-O-(6"-O-p-coumaroyl) glucoside can be prepared from grape raw materials with complex polyphenol components, it has the advantages of large processing capacity and good repeatability, and it is convenient to realize industrialized production.

DESCRIPTION OF EMBODIMENTS

The present application will be further described below in conjunction with the drawings and specific embodiments. It should be understood that these embodiments are only used for illustrating the present application, rather than limiting the scope of the present application. The operation methods without specific conditions in the following embodiments are usually in accordance with conventional conditions or in accordance with conditions recommended by manufacturers.

Example 1

Figure 1:
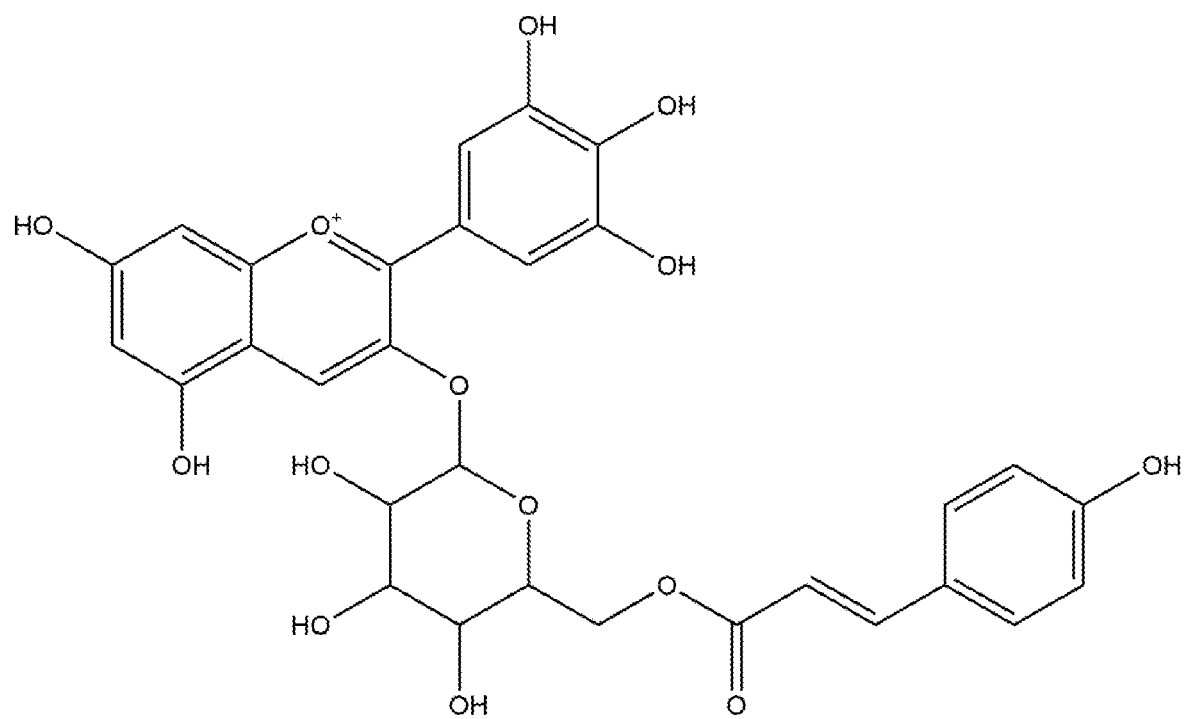
FIG. 1 is a molecular structure diagram of delphinidin-3-O-(6"-O-p-coumaroyl) glucoside.
Figure 2:
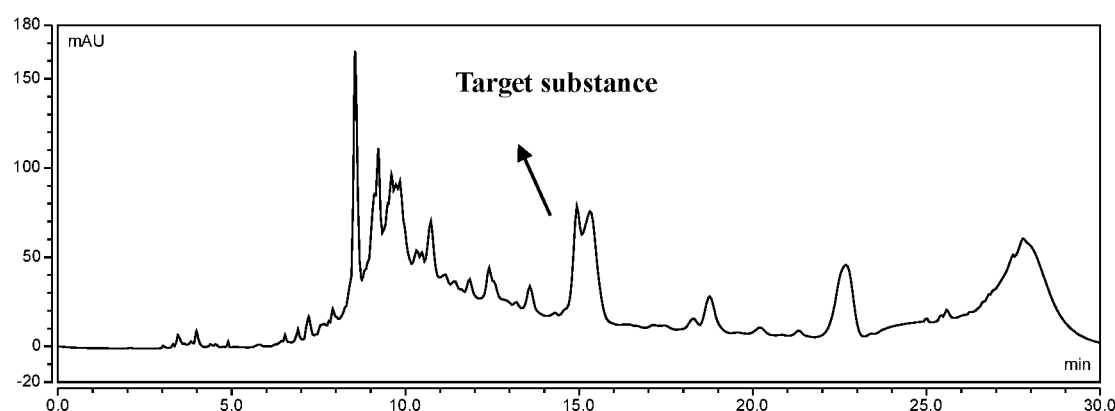
FIG. 2 is a high performance liquid chromatogram of crude grape skin anthocyanin extract in Example 1.

Grapes were washed and peeled to obtain 8 kg of grape skins, a 70% ethanol solution containing 0.5% (v/v) of hydrochloric acid was added according to a material-to-liquid ratio of 1 g:4 mL and was evenly mixed, ultrasonic extraction was carried out for 120 min (the temperature was controlled below 50° C., and it was protected from light), filtration was carried out by using gauze, the filtrate was centrifuged at 4000 rpm for 10 min, and the supernatant was taken. The filter residue was extracted once more in the same way. The filtrates were merged and were filtered again by using a buchner funnel. Vacuum vaporization was performed on the filtrate at 45° C. to remove ethanol, and concentration was performed to obtain crude anthocyanin extract of grape skins. The high performance liquid chromatogram of the crude anthocyanin extract of grape skins is shown in FIG. 2.

Figure 3:
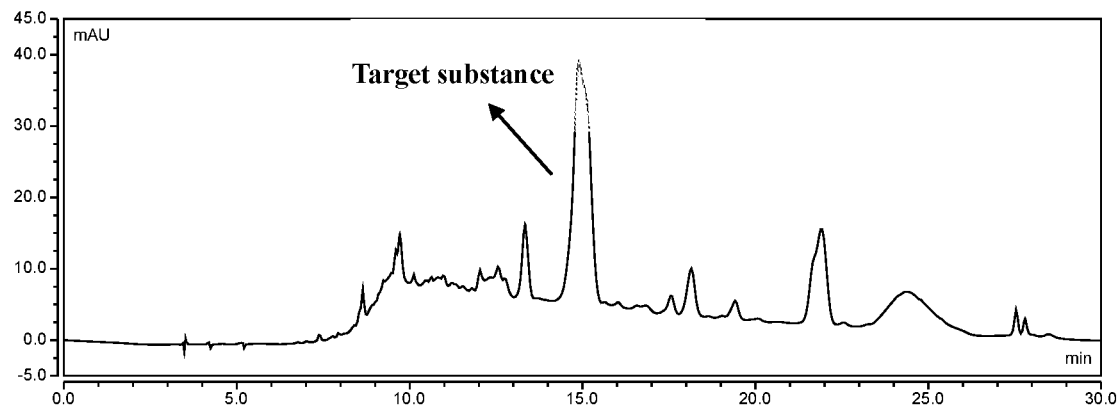
FIG. 3 is a high performance liquid chromatogram of Example 1, containing delphinidin-3-O-(6"-O-p-coumaroyl) glucoside after separation and purification by macroporous resin.

AB-8 macroporous resin was placed in a chromatographic column, and was washed with ethanol, 0.5 mol/L hydrochloric acid solution, 0.5 mol/L sodium hydroxide solution and water in sequence, and the crude anthocyanin extract of grape skins was injected into the chromatographic column at a flow rate of 0.2 BV/h. After sample injection, elution was sequentially performed by using acid water (containing 0.5% of hydrochloric acid), and 5%, 20% and 40% acid ethanol (containing 0.5% of hydrochloric acid) at a dose of 4 times the bed volume, 40% acid ethanol eluent was collected, and vacuum vaporization was performed to remove ethanol. Then, extraction was carried out twice by using ethyl acetate at a ratio of 1:1, the aqueous phase was taken, and proper vacuum vaporization and freeze drying were performed to obtain anthocyanin freeze-dried powder. After separation and purification by the macroporous resin, the high performance liquid chromatogram of a part containing delphinidin-3-O-(6"-O-p-coumaroyl) glucoside is shown in FIG. 3.

For HPLC separation, the Ultimate XB-C18 (7 μm, 21.2× 250 mm) preparative chromatographic column was used. The mobile phase consisted of pure acetonitrile (phase A) and 1.5% (v/v) of formic acid aqueous solution (phase B). The gradient elution method was as follows: 0-4 min, 5%-20% phase A; 4-18 min, 20%-25% phase A; 18-21 min, 25%-35% phase A; 21-24 min, 35%-60% phase A; 24-27 min, 60%-5% phase A; 27-30 min, 5% phase A, the flow rate was 10 mL/min, the column temperature was 30° C., and the detection wavelength was 520 nm. Sample injection was performed after the anthocyanin freeze-dried powder was dissolved, the injection volume was 4 mL, components were collected for 16.5-18.0 min, vacuum concentration was performed, and then freeze drying was performed to obtain a crude product of delphinidin-3-O-(6"-O-p-coumaroyl) glucoside monomer.

Figure 4:
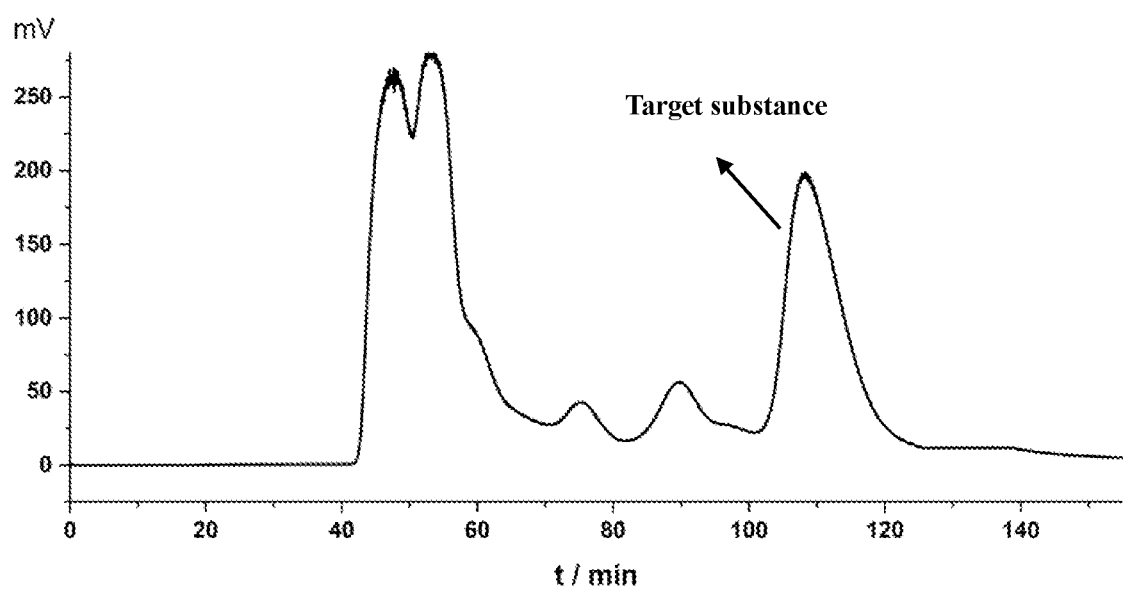
FIG. 4 is a high-speed countercurrent chromatogram in Example 1.
Figure 5:
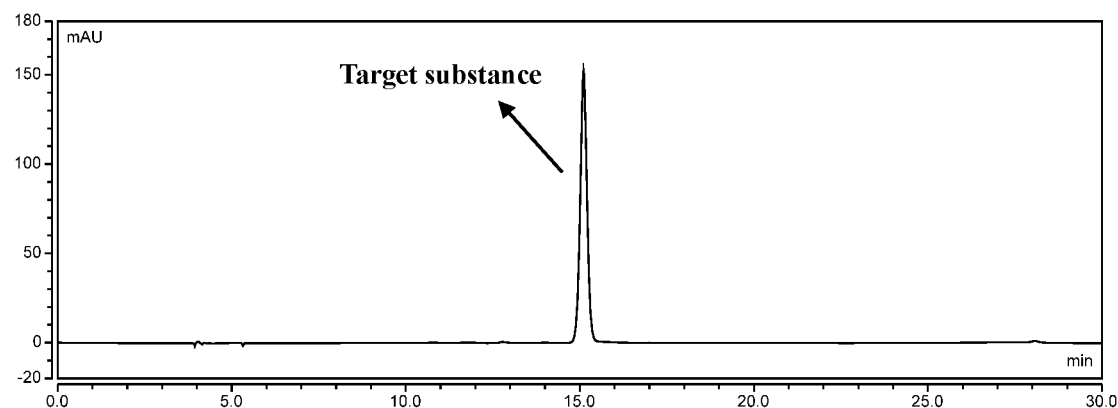
FIG. 5 is a high performance liquid chromatogram of a final product delphinidin-3-O-(6"-O-p-coumaroyl) glucoside in Example 1.

Methyl tert-butyl ether, methanol, water and trifluoroacetic acid were placed in a separating funnel at a volume ratio of 2:2:3:0.001, and after evenly shaking and stewing for 30 min, upper and lower phases were separated and were respectively ultrasonically degassed for 30 min. The instrument temperature of the high-speed countercurrent chromatography system was stabilized at 20° C., the stationary phase was pumped, then the rotation speed was adjusted to 850 r/min, the forward-inlet elution mode were carried out, the mobile phase was injected at a flow rate of 2 mL/min until balance, the crude product of freeze-dried powder was dissolved at a ratio that each 5 mg of freeze-dried powder was dissolved in 1 mL of mobile phase, and sample injection was performed after filtering with a microporous membrane, the single injection volume was 10 mL, detection was performed under an ultraviolet detector, and the detection wavelength was 280 nm. Target peak components were collected for 105-115 min (as shown in FIG. 4), and vacuum concentration and freeze drying were performed to obtain 70 mg of delphinidin-3-O-(6"-O-p-coumaroyl) glucoside, wherein the high performance liquid chromatogram was shown in FIG. 5, the HPLC purity is 98.7%.

Figure 6:
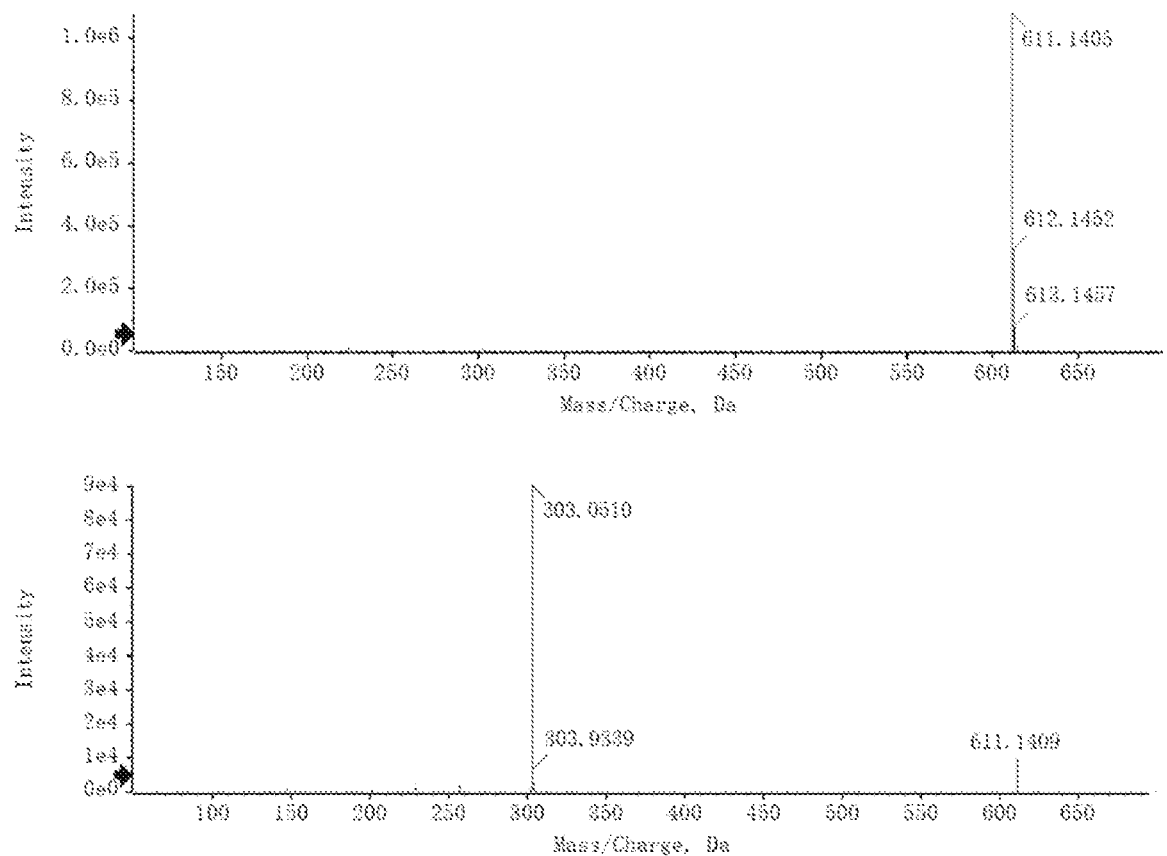
FIG. 6 is a mass spectrum and a tandem mass spectrum of delphinidin-3-O-(6"-O-p-coumaroyl) glucoside in Example 1.

The prepared anthocyanin sample was injected into a mass spectrometer, the sample was analyzed according to the mass spectrum (FIG. 6), and it was confirmed that the mass number of the anthocyanin obtained by separation was normal.

Example 2

Grapes were washed and peeled to obtain 2 kg of grape skins, a 80% ethanol solution containing 0.5% (v/v) of hydrochloric acid was added according to a material-to-liquid ratio of 1 g:6 mL and was evenly mixed, ultrasonic extraction was carried out for 60 min (the temperature was controlled below 50° C., and it was protected from light), filtration was carried out by using gauze, the filtrate was centrifuged at 4000 rpm for 10 min, and the supernatant was taken. The filter residue was extracted once more in the same way. The filtrates were merged and were filtered again by using a buchner funnel. Vacuum vaporization was performed on the filtrate at 45° C. to remove ethanol, and concentration was performed to obtain crude anthocyanin extract of grape skins.

AB-8 macroporous resin was placed in a chromatographic column, and was washed with ethanol, 0.5 mol/L hydrochloric acid solution, 0.5 mol/L sodium hydroxide solution and water in sequence, and the crude anthocyanin extract of grape skins was injected into the chromatographic column at a flow rate of 0.2 BV/h. After sample injection, elution was sequentially performed by using acid water (containing 0.5% of hydrochloric acid), and 5%, 20% and 40% acid ethanol (containing 0.5% of hydrochloric acid) at a dose of 4 times the bed volume, 40% acid ethanol eluent was collected, and vacuum vaporization was performed to remove ethanol. Then, extraction was carried out twice by using ethyl acetate at a ratio of 1:1, the aqueous phase was taken, and proper vacuum vaporization and freeze drying were performed to obtain anthocyanin freeze-dried powder.

For HPLC separation, the Ultimate XB-C18 (7 μm, 21.2× 250 mm) preparative chromatographic column was used. The mobile phase consisted of pure acetonitrile (phase A) and 1.5% (v/v) of formic acid aqueous solution (phase B). The gradient elution method was as follows: 0-4 min, 5%-20% phase A; 4-18 min, 20%-25% phase A; 18-21 min, 25%-35% phase A; 21-24 min, 35%-60% phase A; 24-27 min, 60%-5% phase A; 27-30 min, 5% phase A, the flow rate was 10 mL/min, the column temperature was 30° C., and the detection wavelength was 520 nm. Sample injection was performed after the anthocyanin freeze-dried powder was dissolved, the injection volume was 4 mL, components were collected for 16.5-18.0 min, vacuum concentration was performed, and then freeze drying was performed to obtain a crude product of delphinidin-3-O-(6"-O-p-coumaroyl) glucoside monomer.

Methyl tert-butyl ether, methanol, water and trifluoroacetic acid were placed in a separating funnel at a volume ratio of 2:2:3:0.001, and after evenly shaking and stewing for 30 min, upper and lower phases were separated and were respectively ultrasonically degassed for 30 min. The instrument temperature of the high-speed countercurrent chromatography system was stabilized at 25° C., the stationary phase was pumped, then the rotation speed was adjusted to 850 r/min, the forward-inlet elution mode were carried out, the mobile phase was injected at a flow rate of 2 mL/min until balance, the crude product of freeze-dried powder was dissolved at a ratio that each 5 mg of freeze-dried powder was dissolved in 1 mL of mobile phase, and sample injection was performed after filtering with a microporous membrane, the single injection volume was 10 mL, detection was performed under an ultraviolet detector, and the detection wavelength was 280 nm. Target peak components were collected for 105-115 min, vacuum concentration and freeze drying were performed to obtain 19 mg of delphinidin-3-O-(6"-O-p-coumaroyl) glucoside, and the HPLC purity was 98.2%.

Example 3

Grapes were washed and peeled to obtain 20 kg of grape skins, a 70% ethanol solution containing 0.5% (v/v) of hydrochloric acid was added according to a material-to-liquid ratio of 1 g:4 mL and was evenly mixed, ultrasonic extraction was carried out for 90 min (the temperature was controlled below 50° C., and it was protected from light), filtration was carried out by using gauze, the filtrate was centrifuged at 4000 rpm for 10 min, and the supernatant was taken. The filter residue was extracted once more in the same way. The filtrates were merged and were filtered again by using a buchner funnel. Vacuum vaporization was performed on the filtrate at 45° C. to remove ethanol, and concentration was performed to obtain crude anthocyanin extract of grape skins.

AB-8 macroporous resin was placed in a chromatographic column, and was washed with ethanol, 0.5 mol/L hydrochloric acid solution, 0.5 mol/L sodium hydroxide solution and water in sequence, and the crude anthocyanin extract of grape skins was injected into the chromatographic column at a flow rate of 0.2 BV/h. After sample injection, elution was sequentially performed by using acid water (containing 0.5% of hydrochloric acid), and 5%, 20% and 40% acid ethanol (containing 0.5% of hydrochloric acid) at a dose of 2 times the bed volume, 40% acid ethanol eluent was collected, and vacuum vaporization was performed to remove ethanol. Then, extraction was carried out twice by using ethyl acetate at a ratio of 1:1, the aqueous phase was taken, and proper vacuum vaporization and freeze drying were performed to obtain anthocyanin freeze-dried powder.

For HPLC separation, the Ultimate XB-C18 (7 μm, 21.2× 250 mm) preparative chromatographic column was used. The mobile phase consisted of pure acetonitrile (phase A) and 1.5% (v/v) of formic acid aqueous solution (phase B). The gradient elution method was as follows: 0-4 min, 5%-20% phase A; 4-18 min, 20%-25% phase A; 18-21 min, 25%-35% phase A; 21-24 min, 35%-60% phase A; 24-27 min, 60%-5% phase A; 27-30 min, 5% phase A, the flow rate was 10 mL/min, the column temperature was 30° C., and the detection wavelength was 520 nm. Sample injection was performed after the anthocyanin freeze-dried powder was dissolved, the injection volume was 3 mL, components were collected for 16.5-18.0 min, vacuum concentration was performed, and then freeze drying was performed to obtain a crude product of delphinidin-3-O-(6"-O-p-coumaroyl) glucoside monomer.

Methyl tert-butyl ether, methanol, water and trifluoroacetic acid were placed in a separating funnel at a volume ratio of 2:2:3:0.001, and after evenly shaking and stewing for 30 min, upper and lower phases were separated and were respectively ultrasonically degassed for 30 min. The instrument temperature of the high-speed countercurrent chromatography system was stabilized at 25° C., the stationary phase was pumped, then the rotation speed was adjusted to 850 r/min, the forward-inlet elution mode were carried out, the mobile phase was injected at a flow rate of 2 mL/min until balance, the crude product of freeze-dried powder was dissolved at a ratio that each 10 mg of freeze-dried powder was dissolved in 1 mL of mobile phase, and sample injection was performed after filtering with a microporous membrane, the single injection volume was 15 mL, detection was performed under an ultraviolet detector, and the detection wavelength was 280 nm. Target peak components were collected for 105-115 min, vacuum concentration and freeze drying were performed to obtain 163 mg of delphinidin-3-O-(6"-O-p-coumaroyl) glucoside, and the HPLC purity was 98.2%.

Comparative Example 1

Figure 7:
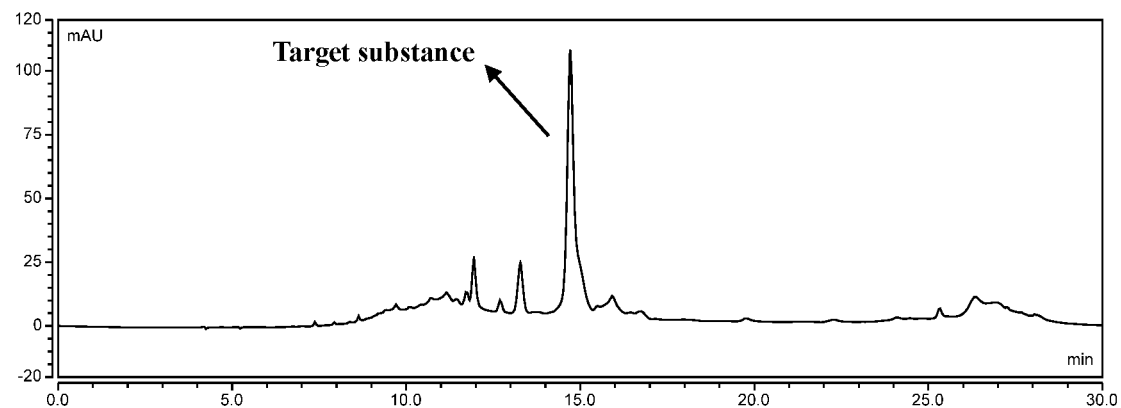
FIG. 7 is a high performance liquid chromatogram of the final product in comparative example 1.

The preparation process was the same as that of Example 1, the only difference was that the purification step via the high-speed countercurrent chromatography was removed, and the other steps remain unchanged. The high performance liquid chromatogram of the final product obtained is shown in FIG. 7, and it can be seen that a mixture of delphinidin-3-O-(6"-O-p-coumaroyl) glucoside was only obtained in the comparative example, and a delphinidin-3-O-(6"-O-p-coumaroyl) glucoside monomer cannot be obtained.

Comparative Example 2

Figure 8:
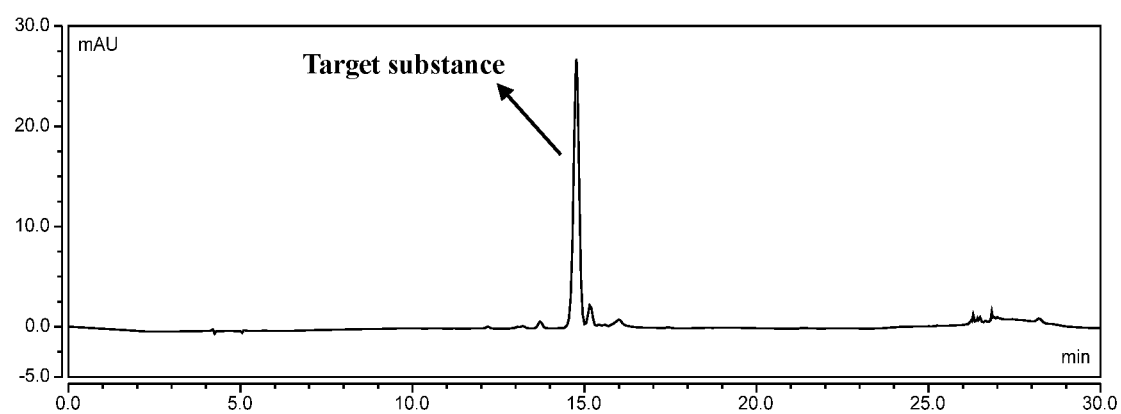
FIG. 8 is a high performance liquid chromatogram of the final product in comparative example 2.

The preparation process was the same as that of Example 1, the only difference was that the flow rate in the purification step via the high-speed countercurrent chromatography was set as 5 mL/min. Tests showed that, although the target component delphinidin-3-O-(6"-O-p-coumaroyl) glucoside was collected, the target component was not completely separated from other anthocyanins and other impurities due to the too fast flow rate, and the purity of the obtained target component was only 90% (FIG. 8).

Comparative Example 3

The preparation process was the same as that of Example 1, the only difference was that the solvent system for separating the high-speed countercurrent chromatography was replaced with a system of n-butanol, methyl tert-butyl ether, methanol, water and trifluoroacetic acid at a ratio of 2:2:1:5:0.001. Tests showed that, the target compound delphinidin-3-O-(6"-O-p-coumaroyl) glucoside was mainly retained in the upper phase, and the target compound was not collected.

Comparative Example 4

The preparation process was the same as that of Example 1, the only difference was that the solvent system for separating the high-speed countercurrent chromatography was replaced with a system of methyl tert-butyl ether, methanol, water and trifluoroacetic acid at a ratio of 2:1:3:0.001. Tests showed that, the target compound delphinidin-3-O-(6"-O-p-coumaroyl) glucoside was not obtained.

Comparative Example 5

The preparation process was the same as that of Example 1, the only difference was that the collection time of the components during the purification process of the preparative liquid chromatography was changed, if the collection time of the components was not within the range of 16.5-18.0 min, components containing delphinidin-3-O-(6"-O-p-coumaroyl) glucoside cannot be obtained. If the collection time of the components includes and was wider than the range of 16.5-18.0 min, it would affect the purity of the final delphinidin-3-O-(6"-O-p-coumaroyl) glucoside monomer obtained by separation.

Comparative Example 6

The preparation process was the same as that of Example 1, the only difference was that the extraction process was changed, such that the acid ethanol solution was not used for extraction, but an ethanol solution containing no acid was used for extraction. The other steps remained unchanged, the yield of the final target product delphinidin-3-O-(6"-O-p-coumaroyl) glucoside monomer was 2 mg/kg of grape skins, which was much lower than 8 mg/kg of grape skins.

In addition, it should be understood that after reading the above descriptions of the present application, those skilled in the art can make various changes or modifications to the present application, and these equivalent forms also fall within the scope defined by the appended claims of the present application.

What is claimed is:

1. A method for separating and preparing delphinidin-3-O-(6"-O-p-coumaroyl) glucoside, comprising:
   using grapes as a raw material, and extracting by an acid ethanol solution, filtering and concentrating to obtain a crude grape skin anthocyanin extract;
   macroporous resin purification: injecting the crude grape skin anthocyanin extract into macroporous resin, and eluting and concentrating to obtain an anthocyanin eluent;
   extraction: extracting the anthocyanin eluent with an organic solvent, concentrating under reduced pressure, and freeze-drying to obtain anthocyanin lyophilized powder;
   purification by preparative liquid chromatography: dissolving the lyophilized anthocyanin powder, injecting the solution into a preparative liquid chromatography system for purification, and detecting with an ultraviolet detector, wherein the specific conditions are as follow:
      mobile phase: phase A is pure acetonitrile, and phase B is a formic acid aqueous solution with a volume percentage of 1%-2% formic acid;
      the gradient elution program is: 0 min-4 min, 5%-20% phase A; 4 min-18 min, 20%-25% phase A; 18 min-21 min, 25%-35% phase A; 21 min-24 min, 35%-60% phase A; 24 min-27 min, 60%-5% phase A; 27 min-30 min, 5% phase A;
      the flow rate is 8 mL/min-10 mL/min, the column temperature is 30° C., and the detection wavelength is 520 nm; and
      collecting the components with retention time of 16.5 min-18.0 min according to the liquid chromatogram, and concentrating under reduced pressure and freeze-drying to obtain the crude product of anthocyanin monomer,
   separation by high-speed countercurrent chromatography: mixing methyl tert-butyl ether, methanol, water and trifluoroacetic acid at a volume ratio of 2:2:3:0.001 to act as a two-phase solvent system, using the upper phase as a stationary phase, and using the lower phase as a mobile phase, pumping the stationary phase and the mobile phase into a high-speed countercurrent chromatographic instrument in turn, after the two phases reach balance in a pipeline, dissolving the crude product of anthocyanin monomer in the mobile phase, injecting the sample, and detecting by the ultraviolet detector, wherein the detection wavelength is 280 nm, collecting the fractions with a retention time of 105 min-115 min, concentrating under reduced pressure, and freeze-drying to obtain a target compound delphinidin-3-O-(6"-O-p-coumaroyl) glucoside.

2. The method according to claim 1, wherein extracting by an acid alcohol solution, filtering and concentrating to obtain the crude anthocyanin extract of grape skins comprises: washing grapes and peeling them, mixing the grape skins with an acid ethanol solution and pulping, ultrasonic extracting below 50° C. and filtrating, and concentrating the filtrate under reduced pressure at 40° C.-50° C. for removing ethanol, so as to obtain the crude anthocyanin extract of grape skins; wherein the material-to-liquid ratio of the grape skins to the acid ethanol solution is 1 g:4 mL-8 mL; in the acid ethanol solution, the volume concentration of ethanol is 50%-80%, the volume concentration of the acid is 0.1%-1%; and the time of the ultrasonic extraction is 40 min-120 min.

3. The method according to claim 2, wherein the acid is selected from at least one of hydrochloric acid, formic acid, or acetic acid in the acid ethanol solution.

4. The method according to claim 1, wherein the method of the macroporous resin purification comprising:
   injecting the crude grape skin anthocyanin extract into the macroporous resin, eluting by sequentially using acid ethanol solutions in which the volume concentration of ethanol is 0, 5%, 20% and 40% each at a dose of 4 times the bed volume (4 BV), collecting acid ethanol eluent in which the volume concentration of ethanol is 40%, and evaporating under reduced pressure at 40° C.-50° C. for removing ethanol to obtain the anthocyanin eluate, wherein the macroporous resin is selected from AB-8, D101, XAD-7, HPD-100 or DM-130, with a specific surface area of 450 m$^2$/g-550 m$^2$/g, an average pore diameter of 10 nm-50 nm, and a particle size range of 0.3 mm-1.25 mm; and the acid ethanol solution is selected from ethanol solutions in which the volume percent concentration of the acid is 0.1%-1.5%, wherein the acid is selected from at least one of hydrochloric acid, formic acid, or acetic acid.

5. The method according to claim 1, wherein the organic solvent used in the step "extration" is ethyl acetate.

6. The method according to claim 1, wherein the liquid chromatographic column is a C18 column, a single injection is 10 mg-40 mg based on the lyophilized anthocyanin powder, and the volume after concentration under reduced pressure is 40%-70% of the volume before concentration.

7. The method according to claim 1, wherein the temperature of the high-speed countercurrent chromatographic instrument is stabilized at 20° C.-30° C., it is at the forward-inlet elution mode, pumping the stationary phase, and the rotating speed is adjusted to 800 r/min-950 r/min, the mobile phase is introduced at a flow rate of 2 mL/min and allowed to be balanced, and the amount of each injection is 30 mg-200 mg based on the crude product of anthocyanin monomer.

\* \* \* \* \*